United States Patent [19]

Jochum et al.

[11] Patent Number: 4,867,790
[45] Date of Patent: Sep. 19, 1989

[54] DENTAL COMPOSITION CONTAINING AN AZIRIDINE COMPOUND AND METHOD OF PREPARATION

[75] Inventors: Peter Jochum, Seefeld; Wolf-Dietrich Zahler, Seefeld-Hechendorf; Oswald Gasser, Seefeld; Günther Lechner, Frieding; Klaus Ellrich, Wörthsee, all of Fed. Rep. of Germany

[73] Assignee: ESPE Stiftung & Co. Produktions- und Vertriebs KG, Seefeld, Fed. Rep. of Germany

[21] Appl. No.: 148,950

[22] Filed: Jan. 27, 1988

[30] Foreign Application Priority Data

Jan. 27, 1987 [DE] Fed. Rep. of Germany ....... 3702233

[51] Int. Cl.[4] .................... C08L 79/00; C08G 73/00
[52] U.S. Cl. ........................ 106/35; 264/16; 264/222; 264/DIG. 30; 433/214; 523/109
[58] Field of Search .............. 264/16, 17, 18, 222, 264/DIG. 30; 523/109; 433/214; 106/35

[56] References Cited

U.S. PATENT DOCUMENTS 3,453,242 7/1969 Schmitt et al. .
4,093,555 6/1978 Schmitt et al. .
4,167,618 9/1979 Schmitt et al. .
4,493,911 1/1985 Schmitt et al. ................. 523/109
4,532,268 7/1985 Jochum et al. ................. 523/109

OTHER PUBLICATIONS

E. S. Gould, Mechanismus and Struktur in der organischen Chemie, (1962), p. 248 et seq.
E. S. Gould, Mechanismus and Struktur in der organischen Chemie, (1962), p. 307 et seq.
J. Am. Chem. Soc., 75, p. 141, (1953).
J. Org. Chem., 34, p. 4071, (1969).

*Primary Examiner*—Paul Lieberman
*Assistant Examiner*—Christine A. Skane
*Attorney, Agent, or Firm*—Birch, Stewart, Kolasch and Birch

[57] ABSTRACT

An ionogenic compound, soluble or dispersible in aziridine compounds is utilized for delaying the polymerization of aziridine compounds initiated by a sulfonium salt. Said ionogenic compounds contain an anion which is more nucleophilic than the anion present in the sulfonium salt employed. Moreover, a preparation for dental purposes is described which contains these components.

19 Claims, No Drawings

DENTAL COMPOSITION CONTAINING AN AZIRIDINE COMPOUND AND METHOD OF PREPARATION

BACKGROUND AND SUMMARY OF THE INVENTION

For the preparation of precise impressions, such as those used in dentistry, and of working models, such as for dental technology, and of temporary denture parts, aziridine-containing substances are polymerized such as those described, for example, in U.S. Pat. Nos. 3,453,242 and 4,093,555. For this purpose the aziridine-containing compounds are commonly used together with fillers, coloring substances and further adjuvants.

Compounds suitable for the initiation of the polymerization reaction are the sulfonium salts known from U.S. Pat. No. 4,167,618 and having an electron-attracting group in the $\beta$ position to the central sulfur atom and a non-nucleophilic anion.

Furthermore, from EP-A No. 0 110 429 imidazoles present in a dissolved form are known as agents for delaying the polymerization of aziridine compounds.

It has been found that with the known systems the processing period of the initiated mixtures cannot be adequately adjusted for several purposes, especially for making very bulky working models, or at high external temperatures. Particularly in such cases it has been found that it is very difficult to combine a long processing period with a rather short setting time. For making a complete jaw impression, the processing period of the initiated mixture should be sufficient, for example, to place the material on an impression tray and into a syringe, eject the material around the prepared tooth stumps, and thereafter to introduce the filled impression tray into the patient's mouth. Only after this moment should the polymerization commence to take place as rapidly as possible in order that the impression can be removed after a short time without any dimensional change, with the time required for this operation still being acceptable for both the dentist and the patient. The situation is similar in the case of intraoral preparations of temporary denture parts or the preparation of jaw models by dental technicians.

It is thus the object of the present invention to provide compounds which are particularly effective in delaying the polymerization reaction of the aziridine compounds initiated by sulfonium salts without substantially prolonging the setting time.

It has been found that ionogenic compounds soluble or dispersible in aziridine compounds prolong the processing period of aziridine compounds blended with sulfonium salt initiators without substantially influencing the setting time, provided said ionogenic compounds contain anions which are more nucleophilic than the anions present in the sulfonium salts employed.

The subject matter of the present invention is thus a preparation for dental purposes containing three spatially separate components, namely, (a) at least one aziridine compound,
(b) at least one sulfonium salt initiator for (a), and
(c) at least one ionogenic compound soluble or dispersible in (a) and having an anion that is more nucleophilic than the anion of (b).

Moreover, the subject matter of the present invention is the use of an ionogenic compound soluble or dispersible in aziridine compounds for delaying the polymerization of aziridine compounds initiated by a sulfonium salt, said ionogenic compound containing an anion that is more nucleophilic than the anion present in the sulfonium salt employed.

Furthermore, the subject matter of the present invention is directed to a process for preparing dental impression compositions ready for use, which are characterized by the homogenously blending of (a) at least one aziridine compound,
(b) at least one sulfonium salt initiator for (a), and
(c) at least one ionogenic compound soluble or dispersible in (a) and having an anion that is more nucleophilic than the anion of (b).

In this context soluble and dispersible means that the compound (c) is soluble in (a), or can be dissolved or dispersed in (a) by conventional measures, e.g., by the addition of solubilizing agents.

The classification of the anions as to their nucleophilic nature is made, for example, in the manner described by E. S. Gould in *Mechanismus and Struktur in der organischen Chemie* published by Verlag Chemie 1962, page 248 et seq. and 307 et seq., or by C. G. Swain, et al., in *J. Am. Chem. Soc.*, 75, page 141 (1953) and A. B. Ash, et al. in *J. Org. Chem*, 34, page 4071 (1969).

The aziridine compounds (a) employed may be the initially mentioned compounds of U.S. Pat. Nos. 3,453,242 and 4,093,555, which compounds are incorporated herein by references. Examples of such compounds include, e.g., polyethers with terminal aziridino groups and bisphenol-A derivatives with terminal aziridino groups.

Suitable sulfonium salt initiators (b) are described in U.S. Pat. No. 4,167,618 and incorporated herein by reference, among which the sulfonium salts containing nitrile or ester groups positioned $\beta$ to the S atom are preferred. Especially preferred initiators are sulfonium salts with fluroborate anions which exhibit high activity as well as excellent stability. The amount of sulfonium salts employed normally ranges from 1 to 8% by weight, based on the weight of the aziridine compounds, such as those described in U.S. Pat. No. 4,093,555 and from 2 to 20% in other aziridine compounds, by weight, based on the weight of the aziridine compounds.

The ionogenic compounds (c) are employed in quantities of 0.1 to 15% by weight, based on the weight of the aziridine compounds. Quantities of from 1 to 10% by weight are especially preferred.

The ionogenic compound (c) is present either as such, primarily if it is present in liquid form, or in dissolved or dispersed form, especially if the melting point is above room temperature. Suitable solvents or dispersants are substances employed in the plastics processing industry as plasticizers, e.g., phthalates and citrates.

The ionogenic compound or the solution or dispersion thereof may be present with fillers or pigments and optionally with additional adjuvants in pasty form. This is advantageous if also the components (a) and (b) are present in a pasty consistency, because in that case the components (a) to (c) can be metered by the length of the paste extrudate (volume) and blended.

The preparation of the ionogenic compounds used according to the present invention is known. A number of substances are available on the market.

By the use of component (c), the polymerization of the aziridine compound (a) initiated by the sulfonium salt (b) can be substantially delayed. By varying the amount of (c), the setting time of (a) can be varied widely.

A further advantage of the preparation of the present invention is offered by the possibility of using highly reactive and highly stable sulfonium salt initiators (b). They preferably have a nitrile substitutent positioned $\beta$ to the central sulfur atom, and a fluoroborate anion.

With the use of sulfonium slats (b) containing a fluoroborate anion, suitable ionogenic compounds(c) are selected from compounds containing anions that are more nucleophilic than the fluoroborate anion. Suitable anions are, for example, the F, I, Br, Cl, sulfonate, sulfate, alyylsulfate, arylsulfate, and carboxylate anions. Especially preferred anions are sulfonate, alkylsulfate, and carboxylate anions, especially benzenesulfonate, xylenesulfonate, p-toluene-sulfonate, ethosulfate, methosulfate, and laurinate anions, as well as fluoride, bromide, chloride and iodide.

The cation of compound (c) normally performs the function of rendering the ionogenic compound soluble in the aziridine compounds. Cations suited for this purpose are, for example, quaternary ammonium and phosphonium, or tertiary sulfonium cations. Especially suitable are quaternary ammonium cations, for example, tetrabutylammonium, ethyl trioctylammonium, butyl trioctylammonium, ethyl triisooctylammonium or ethyltrihexylammonium cations.

Examples for suitable ionogenic compounds (c) in combination with fluoroborate sulfonium salts are: trioctyl ethylammonium xylene sulfonate, triisooctyl methylammonium tosylate, trioctyl butylammonium tosylate, trioctyl ethylammonium benzensulfonate, trioctyl ethylammonium ethosulfate, trioctyl ethylammonium laurylsulfonate, triisooctylammonium ethosulfate, tributyl ethylphosphonium tosylate, triisooctyl ethylammonium trifluoroacetate, dodecyl benzenesulfonic acid potassium salt, tetrabutylammonium laurinate, trihexyl ethylammonium tosylate, trihexyl ethylammonium benzenesulfonate, tetrabutylammonium iodide, tetrabutylammonium bromide, tetrabutylammonium tosylate, tetrabutylammonium trifluoroacetate, triisooctyl ethylammonium-p-tosylate, tetrabutyl phosphonium chloride, phenylethyl disbutyl ethylammonium chloride, triisooctyl methylammonium p-toluenesulfonate, $\beta$-phenylethyl disbutyl methylammonium iodide, methyl trioctylammonium chloride, trioctyl butylammonium bromide.

In case sulfonium salts (b) with p-toluenesulfonate, alkylsulfate or benzenesulfonate anions are employed, suitable retardant substances (c) are, for example, iodide, bromide, chloride and compounds containing similar anions.

DETAILED DESCRIPTION OF THE INVENTION

The following examples are given as being exemplary of the present invention but should not be considered as limiting the scope thereof.

EXAMPLES 1 TO 6

1.0 g of a polyether having terminal aziridino groups and having an average molecular weight of about 6500 and the preparation of which is described in Example 13 of U.S. Pat. No. 3,453,242 is homogeneously blended with 0.08 g $\beta$-(S-lauryl-S-ethylsulfonium)-butyronitrile fluoroborate. At the same time the percentages (% by weight of ionogenic compound (c) listed in the Table 1 are added. Table 1 lists, in the second column, the respective soluble ionogenic compound employed; the last two columns list the time required for gelling and the moment when a hardened bone dry, rubber-elastic composition is obtained. The time periods are calculated in each instance from the moment of blending of the three components.

TABLE 1

| Example No. | Ionogenic Compound | Concentration of Ionogenic Compound (% by weight) | Time up to Gelling (Minute) | Time up to Hardening (Minute) |
| --- | --- | --- | --- | --- |
| 1 | (comparison) | 0 | 2.0 | 4.5 |
| 2 | trihexyl ethylammonium tosylate | 7 | 3.5 | 7.5 |
| 3 | trihexyl ethylammonium benzensulfonate | 5 | 3.0 | 6.5 |
| 4 | tributyl ethylammonium phosphoniumtosylate | 4 | 3.2 | 7.2 |
| 5 | tetrabutylammonium iodide | 3 | 3.2 | 5.2 |
| 6 | tetrabutylammonium bromide | 2 | 4.0 | 6.3 |

EXAMPLES 7 TO 22

For the preparation of an impression composition for dental purposes, 800 g of the difunctional aziridine compound mentioned in Example 1 are masticated with 350 g fine kieselguhr, and 6.4 g 1-lauryl imidazole are added. 1 g of this paste is blended with 0.2 g of a 1:1 mixture of acetyl tributyl citrate and the sulfonium salt used in Example 1. In addition, the % by weight of ionogenic compound (c) (based on the quantity of aziridine compounds employed) listed in Table 2 are added.

TABLE 2

| Example No. | Ionogenic Compound | Concentration of Ionogenic Compound) (% by weight) | Time up to Gelling (Minute) | Time up to Hardening (Minute) |
| --- | --- | --- | --- | --- |
| 7 | (comparison) | 0 | 3.0 | 5.5 |
| 8 | trioctyl ethylammonium ethosulfate | 5 | 4.0 | 8.3 |
| 9 | tetrabutyl ammonium tosylate | 5 | 4.0 | 7.5 |
| 10 | tetrabutyl ammonium trifluoroacetate | 1 | 3.5 | 6.0 |
| 11 | triisooctyl methylammonium tosylate | 5 | 4.0 | 8.0 |
| 12 | trioctyl ethylammonium benzenesulfonate | 5 | 3.6 | 7.2 |
| 13 | tributyl ethylphosphonium tosylate | 3 | 3.7 | 7.2 |
| 14 | triisooctyl | 3 | 3.8 | 7.5 |

TABLE 2-continued

| Example No. | Ionogenic Compound | Concentration of Ionogenic Compound) (% by weight) | Time up to Gelling (Minute) | Time up to Hardening (Minute) |
|---|---|---|---|---|
| | ethylammonium p-tosylate | | | |
| 15 | tetrabutyl phosphonium chloride | 1 | 4.0 | 7.2 |
| 16 | phenylethyl dibutyl ethylammonium chloride | 1 | 4.0 | 6.7 |
| 17 | tetrabutyl ammonium iodide | 3 | 4.25 | 7.6 |
| 18 | tetrabutyl ammonium bromide | 1 | 3.75 | 6.5 |
| 19 | triisooctyl methylammonium p-toluenesulfonate | 4 | 4.0 | 7.7 |
| 20 | β-phenyl ethyl dibutyl methylammonium iodide | 2 | 4.0 | 7.6 |
| 21 | methyl trioctylammonium chloride | 1.5 | 4.0 | 6.7 |
| 22 | methyl trioctylammonium chloride | 2.0 | 4.0 | 7.0 |

We claim:

1. A dental preparation which comprises as three spatially separated components
   (a) at least one polymerizable aziridine compound,
   (b) at least one sulfonium salt initiator for polymerizing said aziridine (a) including a first anion, wherein said initiator (b) is to be employed in an amount of from about 1% to about 20% by weight based on the weight of the aziridine compound, and
   (c) at least one organic ionogenic compound soluble or dispersible in (a) and having a second anion that is more nucleophilic than said first anion of (b), wherein said component (c) is to be employed in an amount of from about 0.1 to about 15% by weight based on the weight of the aziridine compound.

2. The dental preparation according to claim 1, wherein component (b) is a compound containing a fluoroborate anion and component (c) is a compound containing as an anion a member selected from the group consisting of a fluoro, iodo, bromo, chloro, sulfonate, sulfate, alkylsulfate, arylsulfate, and carboxylate anion.

3. The dental preparation of claim 1 wherein the sulfonium salt is present in an amount of from 2 to 20% by weight, based on the weight of the aziridine compound.

4. The dental preparation of claim 2 wherein the sulfonium salt is present in an amount of from 1 to 8% by weight based on the weight of the aziridine compound.

5. The dental preparation according to claim 2, wherein component (c) is a compound containing as an anion a member selected from the group consisting of benzenesulfonate, xylenesulfonate, p-toluenesulfonate, ethosulfate, methosulfate, and laurinate anion.

6. The dental preparation of claim 1 wherein the aziridine compound (a) is a member selected from the group consisting of polyethers with terminal aziridino groups and bisphenol-A derivatives with terminal aziridino groups.

7. The dental preparation of claim 1 wherein the sulfonium salt initiator (b) is a sulfonium salt containing nitrile or ester groups positioned β to the S atom.

8. The dental preparation of claim 1 wherein the ionogenic compounds (c) are employed in an amount of 1 to 10% by weight, based on the weight of the aziridine compounds.

9. A process for preparing a dental composition ready for use which comprises homogeneously blending together
   (a) at least one aziridine compound,
   (b) from about 1 to about 20% by weight based on the weight of the aziridine compound of at least one sulfonium salt initiator for polymerizing said aziridine (a) including a first anion, and
   (c) from about 0.1 to about 15% by weight based on the weight of the aziridine compound of at least one organic ionogenic compound soluble or dispersible in (a) and having a second anion that is more nucleophilic than said first anion of (b).

10. The dental preparation according to claim 1, wherein said component (c) is a member selected from the group consisting of trioctyl ethylammonium xylene sulfonate, triisooctyl methylammonium tosylate, trioctyl butylammonium tosylate, trioctyl ethylammonium benzensulfonate, trioctyl ethylammonium ethosulfate, trioctyl ethylammonium laurylsulfonate, triisooctylammonium ethosulfate, tributyl ethylphosphonium tosylate, triisooctyl ethylammonium trifluoroacetate, dodecyl benzenesulfonic acid potassium salt, tetrabutylammonium laurinate, trihexyl ethylammonium tosylate, trihexyl ethylammonium benzensulfonate, tetrabutylammonium iodine, tetrabutylammonium bromide, tetrabutylammonium tosylate, tetrabutylammonium trifluoroacetate, triisooctyl ethylammonium-p-tosylate, tetrabutyl phosphonium chloride, phenylethyl disbutyl ethylammonium chloride, triisooctyl methylammonium p-toluenesulfonate, β-phenylethyl disbutyl methylammonium iodide, methyl trioctylammonium chloride, and trioctyl butylammonium bromide.

11. The process according to claim 9, wherein component (b) is a compound containing a fluoroborate anion and component (c) is a compound containing as an anion a member selected from the group consisting of a fluoro, iodo, bromo, chloro, sulfonate, sulfate, alkylsulfate, arylsulfate, and carboxylate anion.

12. The process according to claim 9, wherein component (c) is a compound containing as an anion a member selected from the group consisting of benzenesulfontate, xylenesulfonate, p-toluenesulfonate, ethosulfate, methosulfate, and laurinate anion.

13. The process according to claim 9, wherein component (a) is a member selected from the group consisting of polyethers with terminal aziridino groups and bisphenol-A derivatives with terminal aziridino groups.

14. The process according to claim 9, wherein component (c) is a member selected from the group consisting of trioctyl ethylammonium xylene sulfonate, triisooctyl methylammonium tosylate, trioctyl butylammonium tosylate, trioctyl ethylammonium benzensulfonate, trioctyl ethylammonium ethosulfate, trioctyl ethylammonium laurylsulfonate, triisooctylammonium ethosulfate, tributyl ethylphosphonium tosylate, triisooctyl ethylammonium trifluoroacetate, dodecyl benzenesulfonic acid potassium salt, tetrabutylammonium laurinate, trihexyl ethylammonium tosylate, trihexyl ethylammonium benzenesulfonate, tetrabutylammonium iodine, tetrabutylammonium bromide, tetrabutylammonium tosylate, tetrabutylammonium trifluoroacetate, triisooctyl ethylammonium-p-tosylate, tetrabutyl phosphonium chloride, phenylethyl disbutyl ethylammonium chloride, triisooctyl methylammonium p-toluenesulfonate, β-phenylethyl disbutyl methylammonium iodine, methyl trioctylammonium chloride, and trioctyl butylammonium bromide.

15. The process according to claim 11, wherein component (c) is a compound containing as an anion a member selected from the group consisting of benzenesulfonate, xylenesulfonate, p-toluenesulfonate, ethosulfate, methosulfate, and laurinate anion.

16. The process according to claim 11, wherein component (c) is a member selected from the group consisting of trioctyl ethylammonium xylene sulfonate, triisooctyl methylammonium tosylate, trioctyl butylammonium tosylate, trioctyl ethylammonium benzensulfonate, trioctyl ethylammonium ethosulfate, trioctyl ethylammonium laurylsulfonate, triisooctylammonium etosulfate, tributyl ethylphosphonium tosylate, triisooctyl ethylammonium trifluoroacetate, dodecyl benzenesulfonic acid potassium salt, tetrabutylammonium laurinate, trihexyl ethylammonium tosylate, trihexyl ethylammonium benzenesulfonate, tetrabutylammonium iodide, tetrabutylammonium bromide, tetrabutylammonium tosylate, tetrabutylammonium trifluoroacetate, triisooctyl ethylammonium-p-tosylate, tetrabutyl phosphonium chloride, phenylethyl disbutyl ethylammonium chloride, triisooctyl methylammonium p-toluenesulfonate, β-phenylethyl disbutyl methylammonium iodide, methyl trioctylammonium chloride, and trioctyl butylammonium bromide.

17. A dental composition prepared according to the process defined by claim 9.

18. A dental composition prepared according to the process defined by claim 11.

19. A dental composition prepared according to the process defined by claim 16.

* * * * *